United States Patent
Wright et al.

(10) Patent No.: US 7,238,708 B2
(45) Date of Patent: Jul. 3, 2007

(54) GLUCOSE SENSOR

(75) Inventors: Ernest M. Wright, Los Angeles, CA (US); Ana Diez-Sampedro, Los Angeles, CA (US); Bruce A. Hirayama, Los Angeles, CA (US); Hermann Koepsell, Höchberg (DE); Valentin Gorboulev, Höchberg (DE); Christina Osswald, Würzburg (DE)

(73) Assignee: The Regents of the University of California, Oakland, CA (US)

( * ) Notice: Subject to any disclaimer, the term of this patent is extended or adjusted under 35 U.S.C. 154(b) by 71 days.

(21) Appl. No.: 11/078,934

(22) Filed: Mar. 10, 2005

(65) Prior Publication Data

US 2005/0267154 A1    Dec. 1, 2005

Related U.S. Application Data

(60) Provisional application No. 60/552,275, filed on Mar. 10, 2004.

(51) Int. Cl.
*A61K 31/445* (2006.01)
(52) U.S. Cl. .................................... 514/315
(58) Field of Classification Search ................ None
See application file for complete search history.

(56) References Cited

OTHER PUBLICATIONS

Diez-Sampedro et al., "HSGLT3 a human glucose sensor," Experimental Biology 2003, Abstract # 583.20, Apr. 11-15, 2003, San Diego, CA.*
Scheepers et al., "The Glucose Transporter Families SGLT and GLUT: Molecular Basis of Normal and Aberrant Function," J. Parenteral and Enteral Nutrition, vol. 28, No. 5, pp. 364-371, Sep./Oct. 2004.*
Genbank Accession No. NM_014227, Jung, The Sodium/Substrate Symporter Family: Structural and Functional Features, FEBS Lett. 529(1): 73-77 (2002).
Diez-Sampedro et al., A Glucose Sensor Hiding in a Family of Transporters, PNAS, 2003, 100(20): 11753-11758.

* cited by examiner

*Primary Examiner*—Robert A. Wax
(74) *Attorney, Agent, or Firm*—Pamela J. Sherwood; Bozicevic, Field & Francis LLP

(57) ABSTRACT

Methods are provided for the modulation of hSGLT3 protein glucosensor activity. The sensor is expressed in cholinergic neurons that regulate muscle activity, and in tissues including the brain and pacreas. The present invention also provides methods of identifying therapeutic compounds that modify the function of these sensors. Such therapeutic compounds have a functional effect on regulators of muscle activity, including gastrointestinal smooth muscles; on regulation of weight and metabolism; regulation of pancreatic function, including glucagons release; and in taste perception.

2 Claims, 6 Drawing Sheets
(2 of 6 Drawing Sheet(s) Filed in Color)

(A) Identification of hSGLT3-mRNA in human skeletal muscle and human small intestine by RT-PCR (A) Laser-scanning confocal micrographs of immunostaining by the anti-hSGLT3 antibody (red, 1 and 4) and anti-acetylcholine receptor (beta)-subunit (green, 2 and 5) in the intestine (A) The reaction of hSGLT3 antibody in a human skeletal muscle biopsy

SEQUENCE LISTING

```
<160> NUMBER OF SEQ ID NOS: 8

<210> SEQ ID NO 1
<211> LENGTH: 18
<212> TYPE: DNA
<213> ORGANISM: H. sapien

<400> SEQUENCE: 1
aggttatgag agctttac                                                 18

<210> SEQ ID NO 2
<211> LENGTH: 24
<212> TYPE: DNA
<213> ORGANISM: H. sapien
<220> FEATURE:
<221> NAME/KEY: misc_feature
<222> LOCATION: (4)...(4)
<223> OTHER INFORMATION: n = T or C
<220> FEATURE:
<221> NAME/KEY: misc_feature
<222> LOCATION: (10)...(10)
<223> OTHER INFORMATION: n = T or C
<220> FEATURE:
<221> NAME/KEY: misc_feature
<222> LOCATION: (13)...(13)
<223> OTHER INFORMATION: n = T or C
<220> FEATURE:
<221> NAME/KEY: misc_feature
<222> LOCATION: (22)...(22)
<223> OTHER INFORMATION: n = A or G
<220> FEATURE:
<221> NAME/KEY: misc_feature
<222> LOCATION: 7, 16, 19,
<223> OTHER INFORMATION: n = A,T,C or G

<400> SEQUENCE: 2
ccanaanggn ttntcngang tntc                                          24

<210> SEQ ID NO 3
<211> LENGTH: 21
<212> TYPE: DNA
<213> ORGANISM: H. sapien

<400> SEQUENCE: 3
ctcgctggtc gtgatatggc c                                             21

<210> SEQ ID NO 4
<211> LENGTH: 21
<212> TYPE: DNA
```

-continued

```
<213> ORGANISM: H. sapien

<400> SEQUENCE: 4
gccaacatca acgccacagt g                                          21

<210> SEQ ID NO 5
<211> LENGTH: 23
<212> TYPE: DNA
<213> ORGANISM: H. sapien

<400> SEQUENCE: 5
gggacaactt gacaatcagt gcc                                        23

<210> SEQ ID NO 6
<211> LENGTH: 22
<212> TYPE: DNA
<213> ORGANISM: H. sapien

<400> SEQUENCE: 6
tagagttcag gcatagtagc cg                                         22

<210> SEQ ID NO 7
<211> LENGTH: 24
<212> TYPE: DNA
<213> ORGANISM: H. sapien

<400> SEQUENCE: 7
gtcaggaaga aacagatgat ggtg                                       24

<210> SEQ ID NO 8
<211> LENGTH: 21
<212> TYPE: PRT
<213> ORGANISM: H. sapien

<400> SEQUENCE: 8

Glu Glu Lys Ser Gln Glu Glu Thr Asp Asp Gly Val Glu Glu Asp Tyr
 1               5                  10                  15

Pro Glu Lys Ser Cys
            20
```

GLUCOSE SENSOR

This invention was made with Government support under contracts NIH-DK 19567 and NIH-DK 44582 awarded by the National Institutes of Health. The Government has certain rights in this invention.

BACKGROUND OF THE INVENTION

Glucose, in addition to its central role in metabolism, also plays an important role as a signaling molecule in animal and plant cells. Glucose sensing is critical to such diverse physiological phenomena as regulation of metabolism in yeast, photosynthesis in higher plants, and, in mammals, the regulation of food intake, blood glucose levels, and enteric reflexes. Apart from yeast, where homologs of facilitated glucose transporters (Snf3 and Rgt2) have been implicated in glucose sensing, little is known about the molecular mechanisms involved.

A family of proteins that are reported to act as transporters have been described. Human members of the SLC5 gene family include the intestinal and renal glucose transporters (SLC5A1, SLC5A2), the widely distributed inositol and multivitamin transporters (SLC5A3, SLC5A6) and the thyroid iodide transporter (SLC5A5). While a major function of these plasma membrane proteins is secondary active transport in epithelia, they also behave as $Na^+$ uniporters, water and urea channels, and water cotransporters.

A pig SGLT3 expressed in *Xenopus leavis* oocytes behaves as tightly coupled $Na^+$/glucose cotransporter with a lower affinity for glucose and a more restricted sugar specificity than SGLT1 (SLC5A1) clones. The human homolog to pig SGLT3 (hSGLT3, SLC5A4) was identified in the sequencing of chromosome 22. The sequence of the human protein and gene may be accessed at Genbank, NM_014227.

In view of the importance of glucose sensing in food intake, digestion, blood glucose levels, and enteric reflexes, the expression of such sensors is of great interest. The identification and isolation of sensing receptors (including ion channels), and signaling molecules would allow for the pharmacological and genetic modulation of these pathways. For example, availability of sensor and channel molecules would permit the screening for high affinity agonists, antagonists, inverse agonists, and modulators of activity. Such compounds could then be used in the pharmaceutical and food industries.

SUMMARY OF THE INVENTION

The hSGLT3 protein glucosensor plays a role in regulating the activity of cells in response to glucose. The sensor is expressed, for example, in cholinergic neurons that regulate muscle activity. The sensor is also expressed in tissues including the brain and pacreas. The present invention has important implications for understanding molecular sensing and for identifying novel therapeutic compounds that modify the function of these sensors. Such therapeutic compounds have a functional effect on regulators of muscle activity, including gastrointestinal smooth muscles; on regulation of weight and metabolism; regulation of pancreatic function, including glucagons release; and in taste perception.

Intestinal motility is finely regulated by the enteric nervous system, and all activity between and after a meal appears to be regulated by cholinergic neurons. Glucose is important in regulating intrinsic enteric reflexes after a meal. Members of the SGLT gene family may act as glucosensors by conveying information to the cell about the external glucose concentration directly through the membrane potential, or indirectly coupled through another molecule, e.g. G proteins, etc. In muscle cells, an increase in glucose concentration may depolarize the membrane either by $Na^+$/glucose cotransport or by an increased $Na^+$ conductance though SGLT3.

In one embodiment, the present invention provides an isolated mammalian glucose sensor polypeptide, the receptor comprising at least 50% amino acid identity, usually greater than 60% sequence identity and may have 70%, 80% or 90% identity to an amino acid sequence of hSGLT3. In another embodiment, the present invention provides an isolated polypeptide comprising a transmembrane domain of a glucose-sensor, or a channel forming domain, the domain comprising at least 60% amino acid sequence identity, usually greater than 70% identity, and may have 80% or 90% identity to a transmembrane domain sequence selected from the group consisting of hSGLT3.

In another embodiment, the present invention provides a method for identifying a compound that modulates glucose sensing mediated by hSGLT3, including membrane depolarization by $Na^+$/glucose cotransport or increased $Na^+$ conductance. Such methods may comprise the steps of: (i) contacting a test compound with a glucose-sensor polypeptide, and determining the functional effects of the compound on the polypeptides. In one embodiment, the functional effect is determined by measuring changes in membrane potential. In another embodiment, the functional effect is increased $Na^+$ conductance.

Compounds identified by the present methods find use on modulating muscle function and other activities regulated by glucose sensors, including regulation of metabolism and weight; pancreatic function; taste perception, etc. In addition to glucose, compounds that activate SGLT3 include amino sugars and derivatives thereof. Such agonists may be selective for SGLT3, and not activate SGLT1 at physiologically relevant concentrations.

DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE EMBODIMENTS

Figure 1:
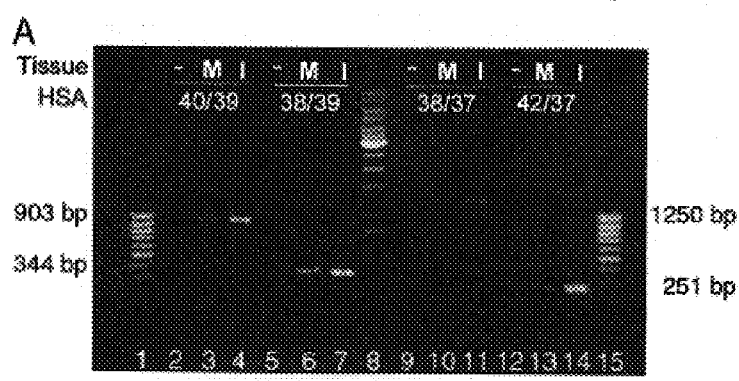
FIG. 1A-B. A. Identification of hSGLT3-mRNA in human skeletal muscle and human small intestine by RT-PCR. Several different pairs of primers were used: lanes 2-4, primer HSA40/primer HSA39 (segment size: 903 bp); lanes 5-7, primer HSA38/primer HSA39 (segment size: 344 bp); lanes 9-11, primer HSA38/primer HSA37 (segment size: 1250 bp); lanes 12-14 primer HSA42/primer HSA 37 (segment size: 251 bp). The primer pairs are separated by introns of the genomic DNA. Lanes 1 and 15, 100 bp ladder (MBI Fermentas), lane 8, 1 kbp ladder (MBI Fermentas), lanes 2, 5, 9, 12 negative controls (−) (water instead of RT-PCR product); lanes 3, 6, 10, 13 skeletal muscle (M), lanes 4, 7, 11, 14 small intestine (I). The PCR products were resolved on agarose gel, blotted and hybridized with hSGLT3-specific oligonucleotides ($\gamma$-$^{32}$P-ATP) to verify the identification of hSGLT3. Amplificates HSA40/HSA39 and HSA38/HSA39 were hybridized with HSA27 (nucleotides 882-1006, forward). Amplificates HSA38/HSA37 and HSA42/HSA37 were hybridized with HSA30 (nucleotides 1878-1855, reverse) (not shown). B. Immunochemical Staining of Western blots with affinity purified antibody against amino acids 576-595 from hSGLT3. Plasma membranes from the small intestine, skeletal muscle and *Xenopus* oocytes were isolated by differential centrifugation. The oocytes were injected with 20 ng of hSGLT3-cRNA (lane 4), 20 ng of hSGLT1-cRNA (lane 5) or water (lane 6). In the Western blots 20 μg of protein was applied per lane. The hSGLT3 antibody recognized a single protein band (~60 kDa) in membranes isolated from whole small intestine (lane 1) and skeletal muscle (lane 3), and from oocytes injected with hSGLT3 cRNA (lane 4), but not from oocytes injected with cRNA from hSGLT1 (lane 5). In lane 2 membranes from small intestine again, but this time the antibody against SGLT3 was blocked by 1 h (37° C.) incubation with 0.1 mg/ml of antigenic peptide.
Figure 1:
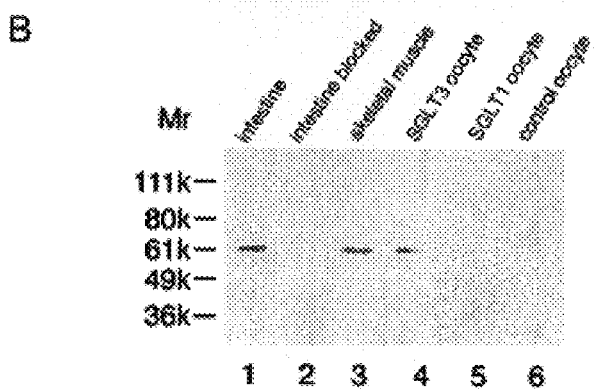

Glucose is important in regulating intrinsic enteric reflexes after a meal; in regulation of metabolism and body weight; in regulation of pancreatic function; and in taste perception.

It is shown herein that the hSGLT3 protein is a glucosensor, which conveys information to the cell about the external glucose concentration directly through the membrane potential, or indirectly coupled through another molecule, e.g. G proteins, etc. Glycosides are also bitter tasting and hGLT3 conveys information to the body about bitter tastes in food.

SGLT3-S1 and its alleles, polymorphic variants and homologs are sensors that affect the membrane potential and/or Na conductance of a cell, in response to extracellular glucose concentrations. The activity of SGLT3 polypeptides can be assessed using a variety of in vitro and in vivo assays to determine functional, chemical, and physical effects, e.g., measuring ligand binding (e.g., radioactive ligand binding), second messengers, ion flux, transcription levels, membrane potential, and the like. Such assays can be used to test for inhibitors and activators of SGLT3.

The glucosensor of the assay will be selected from a polypeptide having a sequence selected from the known SGLT3 polypeptides, e.g. human, pig, etc. or conservatively modified variant thereof. Alternatively, the glucosensor of the assay will be derived from a member of the SGLT family, having sensor activity. Generally, the amino acid sequence identity will be at least 70%, optionally at least 85%, optionally at least 90-95% similar to SGLT3. Optionally, the polypeptide of the assays will comprise a domain of the selected polypeptide, such as an extracellular domain, transmembrane domain, cytoplasmic domain, ligand binding domain, and the like. Either the whole polypeptide or a domain thereof can be covalently linked to a heterologous protein to create a chimeric protein used in the assays described herein.

Modulators of glucosensor activity are tested using selected polypeptides as described above, either recombinant or naturally occurring. The protein can be isolated, expressed in a cell, expressed in a membrane derived from a cell, expressed in tissue or in an animal, either recombinant or naturally occurring. For example, muscle cells or membranes can be used. Modulation is tested using one of the assays described herein.

Ligand binding to SGLT3 whole protein, a domain, or chimeric protein can be tested in solution, in a bilayer membrane, attached to a solid phase, in a lipid monolayer, or in vesicles. In addition to testing membrane potential and Na conductance, binding of a modulator can be tested using, e.g., changes in spectroscopic characteristics (e.g., fluorescence, absorbance, refractive index) hydrodynamic (e.g., shape), chromatographic, or solubility properties.

Receptor-G-protein interactions can also be examined. For example, binding of the G-protein to the receptor or its release from the receptor can be examined. For example, in the absence of GTP, an activator will lead to the formation of a tight complex of a G protein (all three subunits) with the receptor. This complex can be detected in a variety of ways, as noted above. Such an assay can be modified to search for inhibitors. Add an activator to the receptor and G protein in the absence of GTP, form a tight complex, and then screen for inhibitors by looking at dissociation of the receptor-G protein complex. In the presence of GTP, release of the alpha subunit of the G protein from the other two G protein subunits serves as a criterion of activation. An activated or inhibited G-protein will in turn alter the properties of target enzymes, channels, and other effector proteins.

Samples or assays that are treated with a potential glucosensor inhibitor or activator are compared to control samples without the test compound, to examine the extent of modulation. Control samples (untreated with activators or inhibitors) are assigned a relative activity value of 100. Inhibition is considered significant when the activity value relative to the control is 80%, optionally 50% or lower. Activation is achieved when the activity value relative to the control is 150%, preferably 200-500%, or higher.

The effects of the test compounds upon the function of the polypeptides can be measured by examining any of the parameters described above. When the functional consequences are determined using intact cells or animals, one can also measure a variety of effects such as intestinal motility, changes in cell metabolism, and changes in intracellular second messengers, etc.

In another embodiment, transcription levels can be measured to assess the effects of a test compound on signal transduction. A host cell containing the protein of interest is contacted with a test compound for a sufficient time to effect any interactions, and then the level of gene expression is measured. The amount of time to effect such interactions may be empirically determined, such as by running a time course and measuring the level of transcription as a function of time. The amount of transcription may be measured by using any method known to those of skill in the art to be suitable. For example, mRNA expression of the protein of interest may be detected using northern blots or their polypeptide products may be identified using immunoassays. Alternatively, transcription based assays using reporter gene may be used as described in U.S. Pat. No. 5,436,128, herein incorporated by reference. The reporter genes can be, e.g., chloramphenicol acetyltransferase, firefly luciferase, bacterial luciferase, β-galactosidase and alkaline phosphatase. Furthermore, the protein of interest can be used as an indirect reporter via attachment to a second reporter such as green fluorescent protein (see, e.g., Mistili & Spector, Nature Biotechnology 15:961-964 (1997)).

The amount of transcription is then compared to the amount of transcription in either the same cell in the absence of the test compound, or it may be compared with the amount of transcription in a substantially identical cell that lacks the protein of interest. A substantially identical cell may be derived from the same cells from which the recombinant cell was prepared but which had not been modified by introduction of heterologous DNA. Any difference in the amount of transcription indicates that the test compound has in some manner altered the activity of the protein of interest.

Modulators For Glucosensors

The compounds tested as modulators of glucosensors can be any small chemical compound, or a biological entity, such as a protein, amino acid, sugar, nucleic acid or lipid. Alternatively, modulators can be genetically altered versions of glucosensors. Typically, test compounds will be small chemical molecules and peptides.

Modulators of interest may be selective for SGLT3. Such selective modulators include compounds that are agonists for SGLT3, but do not activate SGLT1. It will be understood by those of skill in the art that an agonist activates the glucosensor at a physiologically relevant concentration, e.g. with an affinity of at least about 1 mM, usually an affinity of at least about 100 μM, and may have an affinity of at least about 10 μM, 1 μM or geater. Typically a selective agonist will fail to activate a non-selected protein, e.g. SGLT1, at a concentration of about 100 mM, 50 mM, 10 mM or less.

In one embodiment of the invention, an SGLT3 activator is an amino sugar. Such agonists include, without limitation, molecules having a structure as follows:

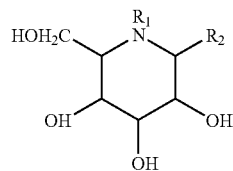

I where $R_1$ is H, $CH_3$, $CH_2CH_3$, etc., including any C1-C6 straight, cyclic or branched alkyl, which can be optionally substituted with one or more heteroatoms;

$R_2$ is H, $CH_2OH$, $CH_2CH_2OH$.

Various stereochemistries may be utilized for the sugar. In one embodiment of interest, the agonist will have the stereochemistry:

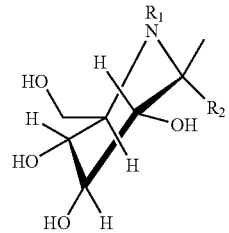

II

In addition to the modulators provided here, screening assays may be performed to assess candidate compounds. Essentially any chemical compound can be used as a potential modulator or ligand in the assays of the invention, although most often compounds can be dissolved in aqueous or organic (especially DMSO-based) solutions are used. The assays are designed to screen large chemical libraries by automating the assay steps and providing compounds from any convenient source to assays, which are typically run in parallel (e.g., in microtiter formats on microciter plates in robotic assays). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs Switzerland), Toronto Research Chemicals (Toronto), Cal-Biochem, and the like.

In one preferred embodiment, high throughput screening methods involve providing a combinatorial chemical or peptide library containing a large number of potential therapeutic compounds (potential modulator or ligand compounds). Such "combinatorial chemical libraries" or "ligand libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, Int. J. Pept. Prot. Res. 37:487-493 (1991) and Houghton et al., Nature 354:84-88 (1991)). Other chemistries for generating chemical diversity libraries can also be used. Such chemistries include, but are not limited to: peptoids (e.g., PCT Publication No. WO 91/19735), encoded peptides (e.g., PCT Publication WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., Proc. Nat. Acad. Sci. USA 90:6909-6913 (1993)), vinylogous polypeptides (Hagihara et al., J. Amer. Chem. Soc. 114:6568 (1992)), nonpeptidal peptidomimetics with glucose scaffolding (Hirschmann et al., J. Amer. Chem. Soc. 114:9217-9218 (1992)), analogous organic syntheses of small compound libraries (Chen et al., J. Amer. Chem. Soc. 116:2661 (1994)), oligocarbamates (Cho et al., Science 261:1303 (1993)), and/or peptidyl phosphonates (Campbell et al., J. Org. Chem. 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., Nature Biotechnology, 14(3):309-314 (1996) and PCTIUS96/10287), carbohydrate libraries (see, e.g., Liang et al., Science, 274: 1520-1522 (1996) and U.S. Pat. No. 5,593,853), small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Tripos, Inc., St. Louis, Mo., 3D Pharmaceuticals, Exton, Pa., Martek Biosciences, Columbia, Md., etc.).

Pharmaceutical Compositions

Active compounds identified by the screening methods described above, analogs thereof (e.g., pharmaceutically acceptable salts), and agonists described herein can serve as the active ingredient in pharmaceutical compositions formulated for the treatment of various disorders as described below. The active ingredient is present in a therapeutically effective amount, i.e., an amount sufficient when administered to substantially modulate the effect of the targeted protein or polypeptide to treat a disease or medical condition mediated thereby.

The compositions can also include various other agents to enhance delivery and efficacy, e.g. to enhance delivery and stability of the active ingredients.

Thus, for example, the compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, buffered water, physiological saline, PBS, Ringer's solution, dextrose solution, and Hank's solution. In addition, the pharmaceutical composition or formulation can include other carriers, adjuvants, or non-toxic, nontherapeutic, non-immunogenic stabilizers, excipients and the like. The compositions can also include additional substances to approximate physiological conditions, such as pH adjusting and buffering agents, toxicity adjusting agents, wetting agents and detergents. The composition can also include any of a variety of stabilizing agents, such as an antioxidant.

When the pharmaceutical composition includes a polypeptide as the active ingredient, the polypeptide can be complexed with various well-known compounds that enhance the in vivo stability of the polypeptide, or otherwise enhance its pharmacological properties (e.g., increase the half-life of the polypeptide, reduce its toxicity, enhance solubility or uptake). Examples of such modifications or complexing agents include sulfate, gluconate, citrate and phosphate. The polypeptides of a composition can also be complexed with molecules that enhance their in vivo attributes. Such molecules include, for example, carbohydrates, polyamines, amino acids, other proteins, ions (e.g., sodium, potassium, calcium, magnesium, manganese), and lipids.

Further guidance regarding formulations that are suitable for various types of administration can be found in Remington's Pharmaceutical Sciences, Mace Publishing Company, Philadelphia, Pa., 17th ed. (1985). For a brief review of methods for drug delivery, see, Langer, Science 249: 1527-1533 (1990).

The pharmaceutical compositions can be administered for prophylactic and/or therapeutic treatments. Toxicity and therapeutic efficacy of the active ingredient can be determined according to standard pharmaceutical procedures in cell cultures and/or experimental animals, including, for example, determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred.

The data obtained from cell culture and/or animal studies can be used in formulating a range of dosages for humans. The dosage of the active ingredient typically lies within a range of circulating concentrations that include the $ED_{50}$ with little or no toxicity. The dosage can vary within this range depending upon the dosage form employed and the route of administration utilized.

The pharmaceutical compositions described herein can be administered in a variety of different ways. Examples include administering a composition containing a pharmaceutically acceptable carrier via oral, intranasal, rectal, topical, intraperitoneal, intravenous, intramuscular, subcutaneous, subdermal, transdermal, intrathecal, or intracranial method.

For oral administration, the active ingredient can be administered in solid dosage forms, such as capsules, tablets, and powders, or in liquid dosage forms, such as elixirs, syrups, and suspensions. The active component(s) can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate. Examples of additional inactive ingredients that may be added to provide desirable color, taste, stability, buffering capacity, dispersion or other known desirable features are red iron oxide, silica gel, sodium lauryl sulfate, titanium dioxide, and edible white ink. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

The active ingredient, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen.

Suitable formulations for rectal administration include, for example, suppositories, which are composed of the packaged active ingredient with a suppository base. Suitable suppository bases include natural or synthetic triglycerides or paraffin hydrocarbons. In addition, it is also possible to use gelatin rectal capsules, which are composed of a combination of the packaged active ingredient with a base, including, for example, liquid triglycerides, polyethylene glycols, and paraffin hydrocarbons.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in vivo use are preferably sterile. To the extent that a given compound must be synthesized prior to use, the resulting product is preferably substantially free of any potentially toxic agents, such as any endotoxins, which may be present during the synthesis or purification process. Compositions for parental administration are also preferably sterile, substantially isotonic and made under GMP conditions.

Uses of Glocosensor Modulators

In light of the pharmacologic activities of SGLT3 related glucosensors, numerous clinical indications are evident. For example, clinical indications for which a modulator may find use include the treatment of inflammatory bowel disease. In another embodiment of the invention, modulators of activity are used in the treatment of gastric or intestinal hypersecretion; gastric atony, urinary retention, reflux esophagitis, motion sickness, anorexia nervosa, nausea and vomiting, e.g. due to chemotherapy, diabetic gastropariesis, etc.

Gastric hypomotility with delayed emptying of liquid and/or solid contents is a component of a number of gastrointestinal disorders, and may be treated with modulators of SGLT3. For a general discussion, see Goodman and Gilman's The Pharmacological Basis of Therapeutics, Chapter 38 (Pergamon Press, Eighth Edition 1990). The symptoms of such disorders may include nausea, vomiting, heartburn, postprandial discomfort, and indigestion. Gastroesophageal reflux is often evident and can give rise to esophageal ulceration; there may also be respiratory symptoms or intense substernal pain that can be confused with asthma or myocardial infarction, respectively. Although the cause is unknown in the majority of patients, gastric stasis or hypomotility is frequently a consequence of diabetic neuropathy; this condition is also often present in patients with anorexia nervosa or achlorhydria or following gastric surgery.

The medical management of patients with gastric hypomotility usually includes the administration of a prokinetic agent. Although antiemetic phenothiazines or bethanechol may provide some relief, these drugs do not accelerate gastric emptying in the vast majority of patients and often produce unacceptable side effects.

Agents that serve to delay gastric emptying have found a place in medicine as well, particularly as diagnostic aids in gastrointestinal radiologic examinations. Such agents are also used to treat various painful gastrointestinal disorders associated with spasm. Modulators of glucosensor proteins described above are useful in view of their pharmacological properties to regulate emptying.

Other clinical indications for which a glucosensor modulating agent may find use include treatment of obesity and regulation of metabolism and body weight. Human obesity is a widespread and serious disorder, affecting a high percentage of the adult population in developed countries. In spite of an association with heart disease, type 11 diabetes, cancer, and other conditions, few persons are able to permanently achieve significant weight loss. The modulating agents are administered to obese patients for purposes of metabolism regulation. Patients may use various criteria for determining obesity. Conveniently, a body mass index (BMI) is calculated, where a person having a BMI greater than 25 is overweight and may considered for treatment with the subject peptides.

In a related embodiment, the treatment of non-insulin-dependent diabetes mellitus (NIDDM) is closely related to the treatment of obesity. NIDDM is a metabolic disease that affects about 5% to 7% of the population in western countries (and 10% of individuals over age 70). It is characterized by hyperglycemia and often accompanied by a number of other conditions, including hypertension, obesity and lipid disturbances. Patients are generally categorized as diabetic or hyperglycemic by measuring the level of glucose in the blood, either directly or by monitoring the level of glycosylated hemoglobin. Treatment is recommended where fasting glucose levels are greater 140 mg/dl, where bedtime glucose is greater than 160 mg/dl, or where $HbA_{cc}$ is greater than 8%. The level of reduction that is desirable depends on the condition of the patient, and the blood glucose levels at the start of treatment, but generally about a 10 to 40% reduction is blood glucose is desirable, usually about a 25 to 35% reduction.

Genetically Altered Cell or Animal Models For Glucosensor Function

Glucosensor encoding nucleic acids can be used to generate transgenic animals or site specific gene modifications in cell lines. Transgenic animals may be made through homologous recombination, where the normal locus is altered. Alternatively, a nucleic acid construct is randomly integrated into the genome. Vectors for stable integration include plasmids, retroviruses and other animal viruses, YACs, and the like.

The modified cells or animals are useful in the study of glucosensor function and regulation. For example, a series of small deletions and/or substitutions may be made in the cospeptin gene to determine the role of different residues in receptor binding or signal transduction. In one embodiment, sequences encoding a glucosensor are used to construct transgenic animal models for disorders where expression of a glucosensor is specifically altered, i.e. reduced, increased, or absent. Specific preferred constructs include anti-sense sequences, which will block the glucosensor expression and expression of dominant negative mutations. A detectable marker, such as lac Z, may be introduced into the locus, where up-regulation of expression will result in an easily detected change in phenotype.

One may also provide for expression of the glucosensor gene or variants thereof in cells or tissues where it is not normally expressed or at abnormal times of development. By providing expression of a protein in cells in which it is not normally produced, one can induce changes in cell behavior, e.g. in the control of cell growth and tumorigenesis.

DNA constructs for homologous recombination will comprise at least a portion of the target gene with the desired genetic modification, and will include regions of homology to the target locus. The regions of homology may include coding regions, or may utilize intron and/or genomic sequence. DNA constructs for random integration need not include regions of homology to mediate recombination. Conveniently, markers for positive and negative selection are included. Methods for generating cells having targeted gene modifications through homologous recombination are known in the art. For various techniques for transfecting mammalian cells, see Keown et al. (1990) Methods in Enzymology 185:527-537.

For embryonic stem (ES) cells, an ES cell line may be employed, or embryonic cells may be obtained freshly from a host, e.g. mouse, rat, or guinea pig. Such cells are grown on an appropriate fibroblast-feeder layer or grown in the presence of leukemia inhibiting factor (LIF). When ES or embryonic cells have been transformed, they may be used to produce transgenic animals. After transformation, the cells are plated onto a feeder layer in an appropriate medium. Cells containing the construct may be detected by employing a selective medium. After sufficient time for colonies to grow, they are picked and analyzed for the occurrence of homologous recombination or integration of the construct. Those colonies that are positive may then be used for embryo manipulation and blastocyst injection. Blastocysts are obtained from 4 to 6 week old superovulated females. The ES cells are trypsinized, and the modified cells are injected into the blastocoel of the blastocyst. After injection, the blastocysts are returned to each uterine horn of pseudopregnant females. Females are then allowed to go to term and the resulting offspring screened for the construct. By providing for a different phenotype of the blastocyst and the genetically modified cells, chimeric progeny can be readily detected.

The chimeric animals are screened for the presence of the modified gene and males and females having the modification are mated to produce homozygous progeny. If the gene alterations cause lethality at some point in development, tissues or organs can be maintained as allogeneic or congenic grafts or transplants, or in culture. The transgenic animals may be any non-human mammal, such as laboratory animals and domestic animals. The transgenic animals may be used in functional studies, drug screening, and the like to determine the effect of a candidate drug on stress responses.

The present invention also provides for kits for screening for modulators of a specific SGLT3. Such kits can be prepared from readily available materials and reagents.

For example, such kits can comprise any one or more of the following materials: SGLT3 nucleic acids or proteins, reaction tubes, and instructions for testing SGLT3 activity. Optionally, the kit contains biologically active SGLT3. A wide variety of kits and components can be prepared according to the present invention, depending upon the intended user of the kit and the particular needs of the user.

EXAMPLES

The following examples are provided by way of illustration only and not by way of limitation. Those of skill in the art will readily recognize a variety of noncritical parameters that could be changed or modified to yield essentially similar results.

Methods

Cloning hSGLT3. Initial RT-PCR was carried out on total RNA from a human colon carcinoma that expresses hSGLT3. The primers were HSA6, designed from a known fragment of hSGLT3 (forward, 5'-AGGTTATGAGAGCTT-TAC-3', position of 697-717, accession # AJ133127) and a degenerate primer SA-DEG designed from a conserved region of the SGLT family (reverse, 5'-CCA(TC)AANGG(TC)TT(TC)TCNGANGT(AG)TC-3', position 1901-1924 of hSGLT3). The 1228 bp fragment obtained was sequenced, and used to obtain the 3' end of hSGLT3 by 3'RACE using RNA from colon carcinoma as a template. The 5' end was obtained using PCR on colon carcinoma cDNA and 5' RACE on Marathon-Ready intestinal cDNA (Clontech). An additional PCR was made to cover nucleotides 8-1878 of hSGLT3. The complete hSGLT3 clone was created by ligation of this PCR product to the 3'-end of hSGLT3 at the HindIII site and cloned into plasmid pRSSP. The cDNA used for functional studies in oocytes was resequenced and the predicted amino acid sequence was identical to that obtained in the genome project.

RT-PCR was carried out on mRNA from human tissues (Clontech). Five different hSGLT3 primers were used:

HSA40 forward, 5'-CTCGCTGGTCGTGATATGGCC-3', position 194-214

HSA39 reverse, 5'-GCCAACATCAACGCCACAGTG-3', position 1076-1096

HSA38 forward, 5'-GGGACAACTTGACAATCAGTGCC-3', position 753-775

HSA37 reverse, 5'-TAGAGTTCAGGCATAGTAGCCG-3', position 1981-2002

HSA42 forward, 5'-GTCAGGAAGAAACAGATGATG-GTG-3', position 1752-1775 and we used primer pairs separated by introns. The PCR products were resolved on agarose gels, blotted and hybridized with γ-$P^{32}$-ATP labeled oligonucleotides.

Immuno-histochemistry. The hSGLT3 specific antibody was raised in rabbits against a peptide (EEKSQEETDDGV-EEDYPEKS-C, residues 576-595), and affinity purified (Sulfolink, Pierce). Blast searches of the Swiss protein data base using the peptide sequence failed to identify other proteins containing this peptide sequence, including nicotinic acetylcholine receptors (see below). The frozen tissue sections, fixed with 3% paraformaldehyde, were incubated for 1 h at 22° C. with the antibody. The reaction of the anti-hSGLT3 antibody was detected with Cy3-coupled secondary antibody against rabbit IgG. The monoclonal antibody for the human AchR β-subunit was from Acris (Hiddenhausen, Germany) and the reaction with acetylcholine receptor was visualized with Cy2-coupled secondary antibody against mouse IgG F(ab')2-fragment. Both secondary antibodies were raised in goat (Dianova, Hamburg, Germany).

The human tissue used for immuno-histochemistry and Western blotting was obtained in accordance with German law under the rules of the Ethics Commission of the University of Wurzburg. Both the duodenal sample (from a 50 year old male gastrectomy patient), and the musculus rectus femoris sample (from a 35 year old tumor patient) were tissues left over from the usual and customary pathological investigations.

Expression of hSGLT3 in oocytes. Stage VI oocytes from *Xenopus laevis* (Nasco, Fort Atkinson, Wis.) were defolliculated and injected with hSGLT3 cRNA and maintained at 18° C. in modified Barth's medium containing gentamycin (5 mg/ml) and penicillin (100 units/ml)/streptomycin (100 μg/ml). Each oocyte was injected with 20 ng of cRNA. Experiments were performed at 22±1° C., 3-9 days after the injection.

Western Blotting. Oocytes were incubated for 3 days after cRNA injection. Plasma membranes from oocytes or tissues were isolated and probed as described (Karbach et al. (2000) *Am. J. Physiol. Renal. Physiol.* 279, F679-F687). Whole tissue samples were homogenized in 280 mM sucrose, 20 mM Tris-HCl pH 7.5, 5 mM EGTA, 5 mM $MgSO_4$ and 1 mM PMSF and centrifuged at 8° C. for 10 minutes at 2,000×g. Membranes were collected by centrifuging the supernatant for 60 minutes at 40,000×g. The resulting pellet was used for Western Blotting. Oocyte membranes were homogenized in 10 mM HEPES pH 7.9, 83 mM NaCl, 1 mM $MgCl_2$ containing 1 mM PMSF, 0.5 ng/ml aprotinin, 0.05 ng/ml leupeptin and 10 mM benzamidine. Debris was removed by centrifugation at 1000×g, and membranes were collected from the supernatant by centrifugation for 20 minutes at 10,000×g. The hSGLT3 antibody dilution was 1:1000 (serum) and the secondary antibody was peroxidase-labeled goat anti-rabbit IgG, and was detected by chemical luminescence (Amersham Buchler). The beta-subunit AchR antibody was used according to the supplier's recommendations. Specificity of the hSGLT3 antibody reaction was verified by showing that no immunohistochemical reaction was observed when the antibodies had been blocked by 1 h (37° C.) incubation with 0.1 mg/ml of antigenic peptide. The beta-subunit AchR antibody did not immunoreact with hSGLT3 expressed in oocytes.

Two electrode-voltage clamp. Oocytes expressing SGLTs and control oocytes were placed in the chamber, impaled with the two electrodes and continuously superfused with the required medium (Loo et al. (1998) *Proc. Natl. Acad. Sci. USA* 95:7789-7794). Membrane potential changes and ionic currents were measured when adding different sugar concentrations. Sugar-specific changes in current were the difference between the values measured with sugar and the preceding value in buffer alone. $Na^+$ buffer contained 100 mM NaCl, 2 mM KCl, 1 mM $CaCl_2$, 1 mM $MgCl_2$ and 10 mM HEPES/tris (pH 7.5). In $Na^+$-free buffer, choline Cl replaced NaCl, and for the experiments at pH 5.0 HEPES/tris was replaced with MES/tris. In some experiments at low pH we simultaneously recorded the intracellular pH of the oocyte using the fluorescent dye BCECF-AM (15, 16). The apparent affinity ($K_{0.5}$) and apparent maximal current ($I_{max}$) were calculated with the equation $[1]=I_{max} \cdot [S]/(K_{0.5}+[S])$, using the non-linear fitting method in SigmaPlot (SPSS, Chicago, Ill.) where [S] is the sugar concentration. The results are illustrated by experiments on single oocytes, but each was representative of at least 3-8 different oocytes.

Uptake experiments. Control oocytes or oocytes expressing a SGLT were superfused with a buffer solution containing either 100 mM NaCl or choline chloride at pH 7.5 or 5 while the plasma membrane potential was clamped at voltages between −50 and −110 mV. When the baseline was stable, D-glucose with tracer [$^{14}$C]-glucose was added. After the sugar was removed from the bathing solution the current returned to the baseline. The oocyte was washed, solubilized and glucose uptake determined using a scintillation spectrometer. Sugar-induced current was obtained by integrating the difference between baseline and the glucose-dependent current. The current, measured simultaneously with sugar uptake, was converted to its molar equivalent of univalent charge. [$^{14}$C]-glucose uptake in non-injected oocytes from the same batch of oocytes was used as a control.

Result

Human SGLT3 was identified as a member of the SLC5 gene family by the Chromosome 22 genome project (GI: 5679464) (Dunham et al. (1999) *Nature* 402, 489-495). The cDNA was cloned and sequenced (Genbank, GI:7263938). The amino acid sequence of the 659 residue protein is identical to that deduced from the genomic sequence. It has 82% amino acid identity to the pig SGLT3 (previously called SAAT1, Kong et al. (1993) *J. Biol. Chem.* 268, 1509-1512), and 70% identity to human SGLT1 $Na^+$/glucose cotransporter (Hediger et al. (1987) *Nature* 330, 379-381). To gain insight into the role of hSGLT3 we examined where the gene is transcribed and the protein is expressed. Northern Blotting and PCR have detected SGLT3 mRNA in pig kidney, intestine, skeletal muscle and spleen. Using RT-PCR we also detected SGLT3-RNA in human skeletal muscle and small intestine. FIG. 1A shows that the mRNA was present in both tissues using different primers. Each primer pair amplified the predicted DNA product from both intestinal and skeletal muscle RNAs. In other experiments, RNase protection assays showed that hSGLT3 was also transcribed in kidney, uterus and testis.

Western blots demonstrated that hSGLT3 mRNA was translated in the human small intestine and skeletal muscle (FIG. 1B). A ~60 kDa band was detected in plasma membranes from oocytes injected with hSGLT3 cRNA (lane 4) and not in the ones injected with hSGLT1 cRNA (lane 5), showing the specificity of the antibody. The antibody identified an identical band in samples from whole small intestine (lane 1) and skeletal muscle plasma membranes (lane 3), and in all cases the immunoreactivity was blocked by the hSGLT3 peptide.

Figure 2:
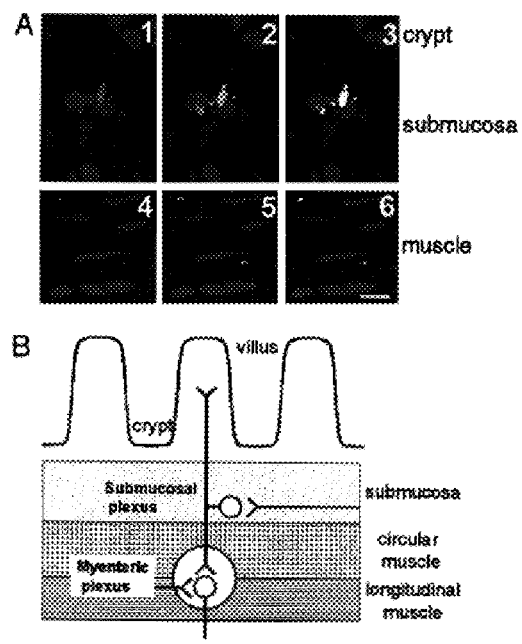
FIG. 2A-B. A. Laser-scanning confocal micrographs of immunostaining by the anti-hSGLT3 antibody (red, 1 and 4) and anti-acetylcholine receptor β-subunit (green, 2 and 5) in the intestine. The images were superimposed to show that the antibodies stain the same structure (yellow, 3 and 6). Reaction products were found below villus crypts in the *plexus submucosus* (1-3 cross section with crypt in the upper right), and in the *plexus myoentericus* (4-6, longitudinal section). The scale bar is 10 μm. B. Cartoon of a cross-section of small intestine showing the major structures and location of the myenteric neurons.

Confocal immunofluorescence microscopy (FIG. 2A) revealed that the hSGLT3 protein in the intestine (red) was restricted to discrete patches of the plasma membrane of cells in the submucosa (A1) and in the longitudinal smooth muscle cells (A4), but no immunoreactivity was detected in the enterocyte. In both locations, the immunoreactively was blocked by the hSGLT3 peptide, and the hSGLT3 immunoreactivity colocalized with the β-subunit of the nicotinic acetylcholine receptor (A2 and A5, the receptor shown in green, and A3 and A6, the superimposed images in yellow). These results suggest that, in the intestine, hSGLT3 is expressed in cholinergic neurons of the submucosal plexus and myenteric plexus (FIG. 2B). In skeletal muscle hSGLT3 is detected in discrete regions of the plasma membrane (FIG. 3A) and colocalized with the acetylcholine receptor (FIG. 3B) suggesting that hSGLT3 is at the neuromuscular junction.

In the brain, the SGLT3 glucosensor is specifically expressed in certain nuclei of the hypothalamus (e.g. ventromedial nucleus) and the amygdale (basomedial and central amygdala).

What role does hSGLT3 play in the physiology of cholinergic neurons and muscle? To address this question we examined functional properties of hSGLT3 in the *Xenopus laevis* oocyte expression system using biochemical and biophysical techniques. Western blots demonstrated that the cRNA injected into the oocytes was translated (FIG. 1B) and freeze-fracture electron microscopy indicated that the protein was efficiently inserted into the plasma membrane. Radioactive tracer assays, however, showed that hSGLT3 expressed in oocytes did not increase the uptake of glucose into oocytes over that of control, non-injected oocytes.

Figure 4:
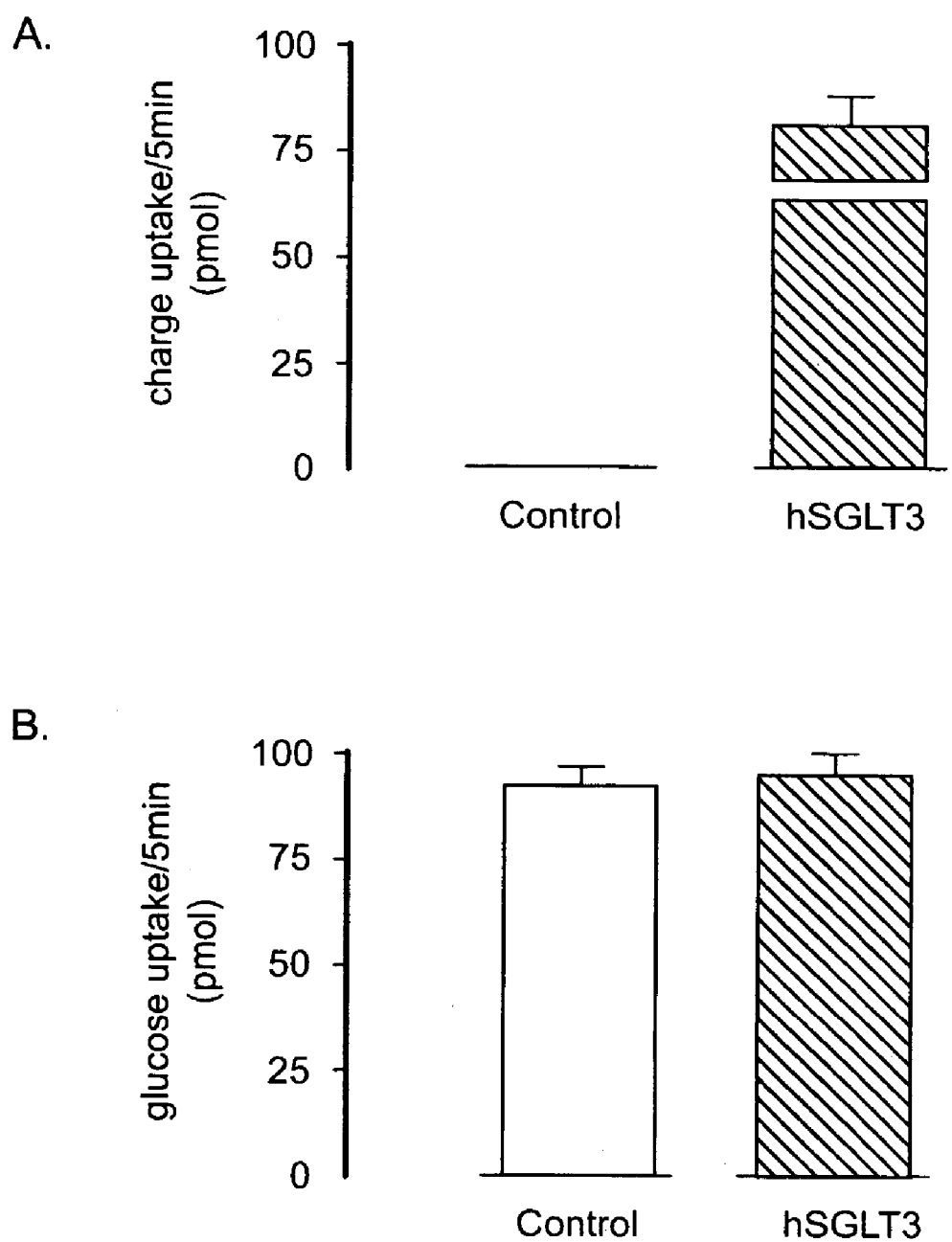
FIG. 4A-B. Sugar induced changes in membrane potential in a single hSGLT3-expressing oocyte. A. In $Na^+$-buffer at pH 7.5, 5 mM glucose or αMDG depolarized the membrane by about 4 mV, while 5 mM galactose had no effect. Phlorizin, a high affinity competitive inhibitor of $Na^+$-glucose cotransport, at a concentration of 250 μM inhibited the membrane depolarization induced by 5 mM glucose. B. Voltage depolarization in response to glucose. The data was fitted to calculate the $K_{0.5}$ (~20 mM glucose) and the maximal depolarization (23 mV) using equation [1]. In 6 experiments $K_{0.5}=60\pm10$ mM and $\Delta Vmax=26\pm9$ mV.

Since freeze-fracture electron microscopy showed that hSGLT3 was inserted in the plasma membrane, we used the two-electrode voltage-clamp to monitor hSGLT3's electrical properties in *Xenopus* oocytes. Exposure of the oocytes expressing hSGLT3 to D-glucose (and the non-metabolized analogue α-methyl-D-glucopyranoside, αMDG) reversibly depolarized the membrane potential (FIG. 4A). This depolarization was specific for D-glucose and αMDG, and was blocked by 250 μM phlorizin. Phlorizin is a specific, competitive inhibitor of pig SGLT3 (Mackenzie et al. (1996) *J. Biol. Chem.* 271, 32678-32683). D-galactose, D-fructose and mannitol had no effect on the membrane potential at concentrations as high as 100 mM. The glucose-induced depolarization saturated with increasing glucose concentrations with an apparent $K_m$ of 20 mM and the maximum depolarization ($\Delta V_m$) was 23 mV (FIG. 4B). This suggests that glucose induced an ionic current through hSGLT3.

Figure 5:
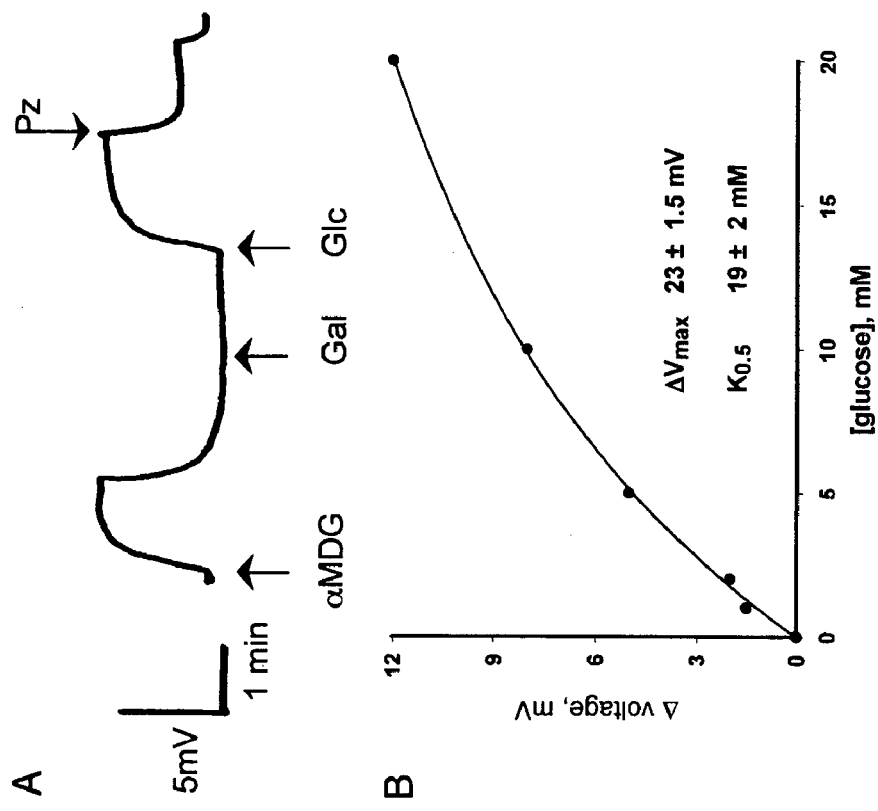
FIG. 5A-B. Effect of membrane potential and pH on sugar-induced current in an hSGLT3 expressing oocyte. The figure shows the currents induced by 25 mM αMDG in $Na^+$ buffer at neutral and acidic pHs and in buffer without $Na^+$ at pH 5 at voltages ranging from +50 mV to −90 mV.

We measured the hSGLT3 currents in oocytes under voltage-clamp conditions and determined the effect of membrane potential on the sugar-dependent current. FIG. 5 shows that αMDG-dependent hSGLT3 currents: a) did not reverse at positive membrane potential; b) increased from +50 to −90 mV; and c) increased on lowering the pH to 5 in the presence or absence of Na+. The sugar concentration dependence of the currents was also recorded. At −150 mV the maximum current at the saturating sugar concentration ($I_{max}$) was 122±20 (n=5) nA and the apparent sugar affinity ($K_{0.5}$) was 36±6 (n=5) mM. There were no sugar-induced currents in the absence of Na+ indicating that Na+ carried the inward current. In four of these oocytes at pH 5 the $I_{max}$ was 1725±99 nA and the $K_{0.5}$ 41±7 mM at pH 5 in NaCl, and the $I_{max}$ 2385±651 nA and the $K_{0.5}$ 131±22 mM in Choline Cl.

This data indicates that H+ carry the sugar current at pH 5 and this is supported by measurement of $^{24}$Na uptakes and intracellular pH: there was no increase in Na+ uptakes at pH 5 but there was a sugar dependent acidification of the cytoplasm.

Figure 6:
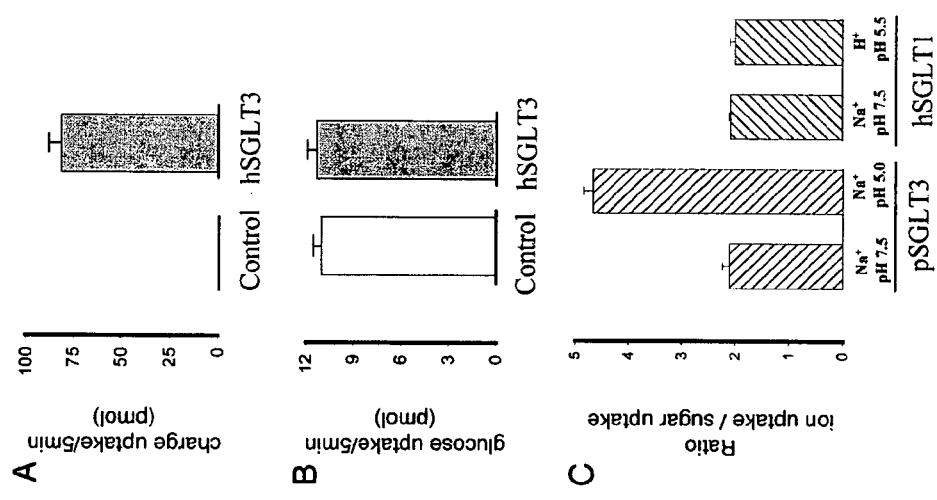
FIG. 6A-C. Sugar uptake is not coupled to cation uptake through SGLT3. Sugar-induced current (A) and glucose uptake (B) were simultaneously measured in the same hSGLT3-expressing (hSGLT3) and in non-injected oocytes (control). The membrane was voltage-clamped at −70 mV, and the experiment was carried in $Na^+$ buffer at pH 5. A. In control oocytes 2 mM glucose did not induce any current, while in hSGLT3 expressing oocytes a sugar dependent current equivalent to univalent positive charge of 81±7 pmol per 5 minutes was recorded. B. Glucose uptakes were recorded in the same oocytes used to measure the currents in FIG. 6A. The glucose uptake in the hSGLT3 oocytes was identical to that in control oocytes (P>0.5). The data is from 5 hSGLT3-expressing and 5 control oocytes. C. Ratio of positive ion uptake and sugar uptake in pSGLT3-and hSGLT1-expressing oocytes. These experiments were carried out as described for hSGLT3 (FIG. 6A,B). In hSGLT1-expressing oocytes, the ratio in $Na^+$ at neutral pH is 2.1±0.04 (n=4) and at acidic pH in $H^+$ is 2±0.1 (n=7) (Taken from Quick et al. 2001). In pSGLT3-expressing oocytes show the same ratio positive charge/sugar uptake at neutral pH: 2.1±0.1 (n=12), but at acidic pH the ratio increases to 4.7±0.2 (n=6).

We examined the relationship between sugar and the inward ion currents through hSGLT3 by simultaneously measuring the radiotracer sugar uptake and sugar-induced currents. Sugar uptakes were identical in control oocytes and those expressing hSGLT3 in the absence or presence of Na+ at pH 7.5 and 5. FIG. 6 illustrates experiments performed in oocytes in Na+ at pH 5. After the baseline current was recorded in the absence of sugar, 2 mM D-glucose containing tracer $^{14}$C-D-glucose was added and the sugar-induced currents were continuously recorded for 5 minutes. In each oocyte we compared uptake of glucose and the cation uptake (calculated from the integrated sugar induced current as the net monovalent charge uptake). D-glucose uptakes were identical in hSGLT3 and control (non-injected) oocytes (11±0.5 and 11±0.6 pmoles, n=5 FIG. 6B). No cation uptakes were induced by glucose in control oocytes, whereas the cation uptake was 81±7 pmoles, n=5 in hSGLT3 oocytes (FIG. 6A). With this cation uptake we would expect a glucose uptake of 40 pmoles if there were a 2/1 coupling between cation and sugar transport as in SGLT1. Since the glucose uptake did not increase above that of the control oocytes (FIG. 6B), we conclude that hSGLT3 is not a glucose cotransporter.

To validate these observations we repeated the experiments with oocytes expressing hSGLT1 and pig SGLT3 (FIG. 6C). The results with both hSGLT1 and pig SGLT3 at pH 7.5 confirmed the 2/1 coupling between ion and sugar transport. While hSGLT1 remained strictly coupled at acid pH, pig SGLT3 became uncoupled at pH 5, i.e. the ratio of ion to sugar uptake increased to 5 (FIG. 6C).

The activation energy ($E_a$) for the sugar-induced hSGLT3 current was determined by measuring the glucose-induced currents in the presence and absence of Na+ at pH 5 at 10, 22 and 28° C. in the same oocyte. Arrhenius plots of the currents obtained in the presence and absence of Na+ gave $E_a$s for the glucose-induced current of ~9 Kcal/mol, much lower than expected for cotransport [26 Kcal/mole (3)]. To further characterize the glucose-induced currents through hSGLT3 we also recorded the effect of cytoplasmic pH on the IN curves in the absence of Na+ at an external pH of 5. In two experiments, we recorded the 100 mM αMDG currents from +50 to −150 mV before and after acidification of the cytoplasm using a 50 mM K acetate pulse. In both, the I/V curves shifted by −50 mV, similar to the D204N hSGLT1 mutant, which behaves as a glucose gated ion channel. These results indicate that the sugar-induced currents through SGLT3 have properties more in common with channels than transporters.

Figure 3:
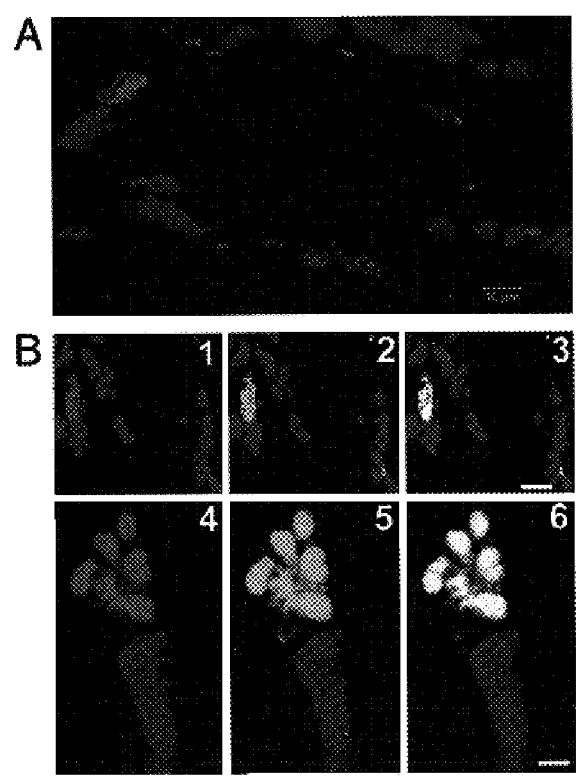
FIG. 3A-B. A. Panel shows the reaction of hSGLT3 antibody in a human skeletal muscle biopsy. The nuclei are stained with DAPI (blue). B. Immunostaining by the anti-hSGLT3 antibody (red, 1 and 4) and the anti-acetylcholine receptor β-subunit antibody (green, 2 and 5) in skeletal muscle. Panel 3 and 6 show that both antibodies stain the same structure. The scale bar is 10 μm in 3 and 2 μm in 6.

To determine the function of a new member of the SLC5 gene family, SGLT3, we have cloned the cDNA, determined where the gene is transcribed and the protein is expressed, and expressed the membrane protein in a heterologous expression system. The amino acid sequence encoded in the cDNA was identical to that predicted from the genomic sequence, and transcripts were detected in tissues including the small intestine and skeletal muscle. In the intestine the protein is found in cholinergic neurons of the submucosal and myenteric plexuses (see FIG. 2) and in skeletal muscle at the neuromuscular junction (FIG. 3). Unlike other members of the family, SGLT3 is not a glucose transporter when expressed in oocytes. However, glucose does produce a phlorizin sensitive inward current that depolarizes the membrane potential by up to 50 mV. The low sugar affinity of the human SGLT3 at pH 7.5 (apparent affinity ~60 mM) means that the depolarization in membrane potential is a linear function of glucose concentration in the physiological range (2-12 mM). We speculate that variations in plasma membrane glucose concentration modulate membrane potential in cholinergic neurons in the enteric nervous system and at the neuromuscular junction in skeletal muscle. The actual magnitude of the responses will depend on the density of SGLT3 proteins, the native conductance of the membranes, and whether or not SGLT3 is coupled to any other protein.

Intestinal motility in both rodents and man is finely regulated by the enteric nervous system, and all activity between and after a meal appears to be regulated by cholinergic neurons. The importance of glucose in regulating intrinsic enteric reflexes after a meal is well recognized. Electrophysiological recordings from guinea pig enteric neurons demonstrated that 77% were glucose sensitive. Two thirds of these neurons hyperpolarized (~5 mV) and their spontaneous electrical discharge were inhibited by the removal of glucose from the extracellular medium. This suggests that the modulation of intestinal motor reflexes following a meal is due to the effects of glucose on these enteric neurons. It was postulated that the glucose sensitivity is mediated by ATP-sensitive K-channels. Our results point to a more direct role of glucose through SGLT3, and are reinforced by our observation that the effect of glucose on the mechanical activity of guinea pig ileum is blocked by phlorizin, the specific blocker of SGLT proteins.

While glucose responsive cells are widely distributed throughout the body, from the hypothalamus to endocrine cells, little is known about the glucosensors in either animal or plants. In yeast, homologs of the facilitated glucose transporters (GLUTs) have been implicated in glucose sensing and this has led to the hypothesis that glucosensors may have evolved from proteins with a glucose-binding site by acquiring a regulatory site for signal transduction. Our results suggest that members of the SGLT gene family may also act as glucosensors by conveying information to the cell about the external glucose concentration directly through the membrane potential, or indirectly coupled through another molecule such as a G protein. As glucosensors the critical factor is not whether the SGLT is a $Na^+$/glucose cotransporter or a glucose-sensitive ion channel, but where the gene is expressed. The SGLTs are expressed in many different cell types ranging from epithelia to neurons, and we show here that SGLT3 is in excitable cells. Thus in skeletal muscle, human or pig, an increase in glucose concentration will depolarize the membrane either by $Na^+$/glucose cotransport or by an increased $Na^+$ conductance though SGLT3.

There is independent evidence that SGLTs are intimately involved in glucosensing in both the central nervous system and gastrointestinal tract. Hypothalamic glucosensing neurons have been implicated in the regulation of food intake and body weight, and these neurons respond to changes in glucose concentration by changes in membrane potential and firing rate. While ATP-sensitive K+ channels may mediate these responses, no changes in ATP concentrations were detected. SGLTs may mediate a change in membrane potential; supported by the observations that phlorizin increases food intake in when injected into the cerebrospinal fluid, and blocks the glucose mediated increase in firing rate of glucose-responsive neurons in the hypothalamus.

Additional evidence comes from studies of Glucagon-Like Peptide-1 secretion from neuroendocrine cells. The non-metabolized sugar αMDG stimulates GLP-1 peptide secretion in a $Na^+$-dependent and phlorizin-sensitive manner. αMDG increases the membrane conductance, depolarizes the membrane potential, and increases action potential frequency.

Nature, therefore, seems to be conservative in her approach to the genome: small modifications in structure can result in large changes in function (cotransporter to channel);

and changes in the location of gene expression may change the physiological role (from epithelial transporter to neuronal glucosensor). Successful protein designs may thus be modified to serve diverse purposes, e.g. the SGLTs are cotransporters, uniporters, glucosensors, water channels and water transporters, or the proteins may be expressed in locations where "secondary" functional properties are exploited.

There are functional differences between the human and pig SGLT3 proteins. When expressed in *Xenopus laevis* oocytes pig SGLT3 behaves as a low-affinity Na/glucose cotransporter with a greater selectivity for sugars than SGLT1. $Na^+$ and glucose transport are tightly coupled at neutral pH, but at pH 5 ion transport is uncoupled from sugar transport (FIG. 6C). Ion transport through human SGLT3 is totally uncoupled to sugar transport at pH 7.5 and 5, but the sugar selectivity of both proteins are quite similar (D-glucose~αMDG>>>D-galactose). The functional differences between human and pig SGLTs are a matter of degree and become moot if indeed the pig protein is expressed in cholinergic neurons in the small intestine and at the neuromuscular junction of skeletal muscle.

In summary, hSGLT3 is expressed in cholinergic neurons of the small intestine and in skeletal muscle at the neuromuscular junctions and this together with the phenotype of hSGLT3 expressed in oocytes, demonstrates that this membrane protein is a glucosensor involved in the regulation of muscle activity. The pig isoform is also expressed in the small intestine and skeletal muscle, but the cellular location of the protein is unknown. It is also possible that the pig protein is expressed in the enteric nervous system and the neuromuscular junction, where it too behaves as a glucosensor. In this case $Na^+$/glucose cotransport would also depolarize the membrane potential and thereby regulate muscle activity. This study points to the hitherto unexpected role of SGLTs in regulating muscle activity, and highlights the importance of not only determining the function of new genes in a family but also the cellular location of the protein.

Example 2

Modulators of SGLT3 Activity

Using the techniques described above, a two-electrode voltage-clamp was used to monitor hSGLT3's electrical properties in *Xenopus* oocytes. The oocytes were exposed to candidate compounds, and the depolarization of membrane potential was recorded. As described above, exposure of the oocytes expressing hSGLT3 to D-glucose (and the non-metabolized analogue α-methyl-D-glucopyranoside, αMDG) reversibly depolarized the membrane potential. This depolarization was specific for D-glucose and αMDG, and was blocked by 250 µM phlorizin. The glucose-induced depolarization saturated with increasing glucose concentrations with an apparent $K_m$ of 20 mM and the maximum depolarization ($\Delta V_m$) was 23 mV.

D-galactose, D-fructose and mannitol had no effect on the membrane potential at concentrations as high as 100 mM. Other compounds that failed to affect the membrane potential at these concentrations were 3-deoxy-D-glucose and 3-D-deoxy-D-glucose.

Of particular interest is the finding that amino sugars activate SGLT3, but do not interact with Na/glucose transporters, such as SGLT1.

Deoxynojirimycin and N-(n-ethyl)deoxynojirimycin were found to activate SGLT2 with affinities in the 500 nanomolar to 2 micromolar ranges. The responses to the amino sugars are specific (no effects at 30 mM on control cells and those expressing SGLT1), and are blocked by phlorizin.

Other amino sugar derivatives, e.g. N (n-butyl) deoxynojirimycin may find use in increasing the blood brain barrier permeability to these agonists.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method of selectively activating an SGLT3 glucosensor, the method comprising:
contacting a cell expressing said SLGT3 glucosensor with an agonist having a structure:

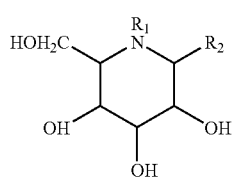

I where $R_1$ is H, $CH_3$, $CH_2CH_3$, or any C1-C6 straight, cyclic or branched alkyl, optionally substituted with one or more heteroatoms; and
$R_2$ is H, $CH_2OH$, $CH_2CH_2OH$.

2. The method according to claim 1, wherein said agonist has the stereochemistry:

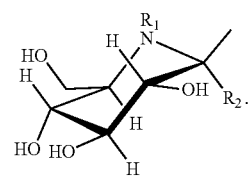

II

* * * * *